United States Patent
Bokros et al.

[11] Patent Number: 6,059,826
[45] Date of Patent: May 9, 2000

[54] TRILEAFLET HEART VALVE

[75] Inventors: Jack C. Bokros; Jonathan C. Stupka; Robert B. More, all of Austin, Tex.

[73] Assignee: Medical Carbon Research Institute, LLC, Austin, Tex.

[21] Appl. No.: 09/064,614

[22] Filed: Apr. 22, 1998

[51] Int. Cl.[7] ........................................... A61F 2/24
[52] U.S. Cl. ................................................. 623/2
[58] Field of Search ................................. 673/2, 900

[56] References Cited

U.S. PATENT DOCUMENTS

| | | |
|---|---|---|
| 4,276,658 | 7/1981 | Hanson et al. . |
| 4,363,142 | 12/1982 | Meyer . |
| 4,364,127 | 12/1982 | Pierce et al. ........................... 623/2 |
| 4,373,216 | 2/1983 | Klawitter . |
| 4,451,937 | 6/1984 | Kalwitter . |
| 4,689,046 | 8/1987 | Bokros . |
| 4,820,299 | 4/1989 | Philippe . |
| 5,123,918 | 6/1992 | Perrier et al. . |
| 5,123,920 | 6/1992 | Bokros . |
| 5,147,391 | 9/1992 | Lane ...................................... 623/2 |
| 5,152,785 | 10/1992 | Bokros et al. . |
| 5,171,263 | 12/1992 | Boyer et al. . |
| 5,197,980 | 3/1993 | Gorshkov et al. .................... 623/2 |
| 5,207,707 | 5/1993 | Gourley . |
| 5,314,467 | 5/1994 | Shu . |
| 5,354,330 | 10/1994 | Hanson et al. . |
| 5,376,111 | 12/1994 | Bokros et al. . |
| 5,628,791 | 5/1997 | Bokros et al. . |
| 5,641,324 | 6/1997 | Bokros et al. . |

FOREIGN PATENT DOCUMENTS

| | | | |
|---|---|---|---|
| 0 790 043 A2 | 8/1997 | European Pat. Off. ................. 623/2 |
| WO 88/02247 | 9/1986 | WIPO . |

*Primary Examiner*—David H. Willse
*Attorney, Agent, or Firm*—Fitch, Even, Tabin & Flannery

[57] ABSTRACT

A trileaflet heart valve includes a generally annular valve body having an interior wall of nominally circular cross-section into which three wedge-shaped projections radially extend to provide three pairs of flanking flat surfaces between which three leaflets are pivotally supported. The valve body has an outwardly flaring upstream entrance end that, together with the configuration of the leaflets, assures streamlined flow and low transvalvular pressure drop. Wing sections extend laterally in both directions at angles between about 30° and 50° from flat central sections of the leaflets to create V-shaped cross-section leaflet bodies having short flat edge sections along the lateral edges of both wing sections that create a wide open central flow passageway. The three leaflets assume an orientation parallel or nearly parallel to the central axis in full open position. Leaflet movement from open to closed position is partially defined by upstream retainers aligned with the flat central sections of each leaflet and by surfaces formed in or on the side walls of the projections along which the leaflets slide. Radially interior edges of the leaflets are tapered to effectively eliminate cavitation.

16 Claims, 8 Drawing Sheets

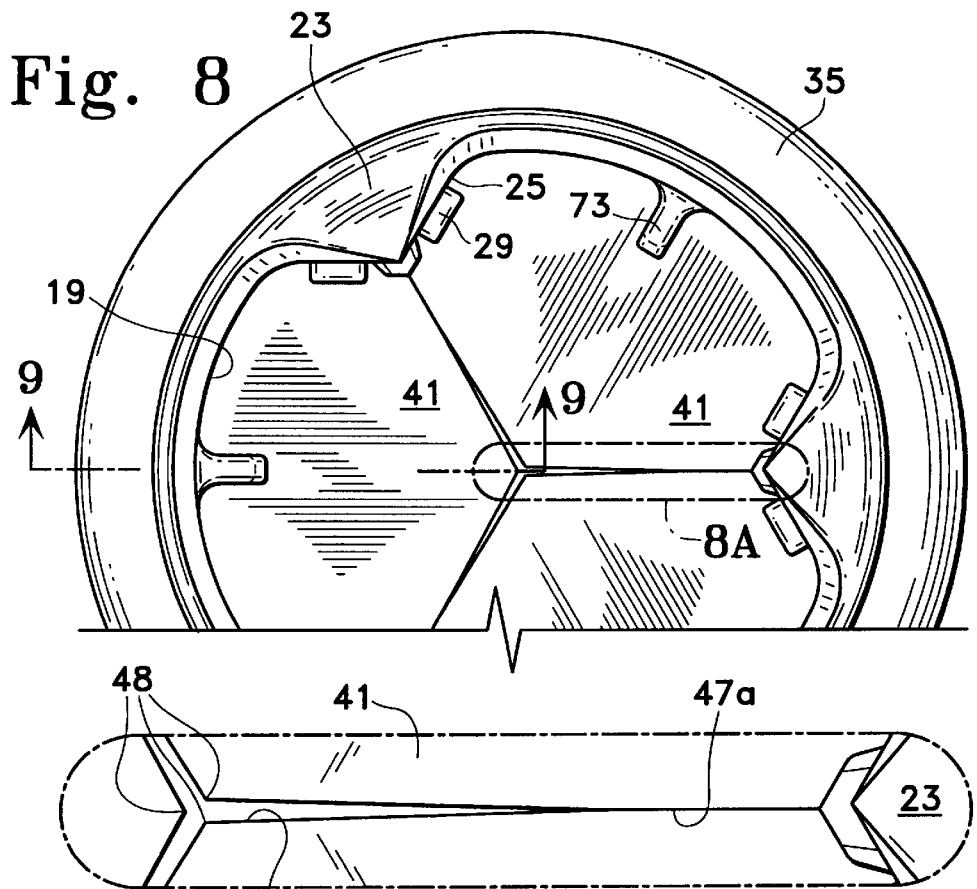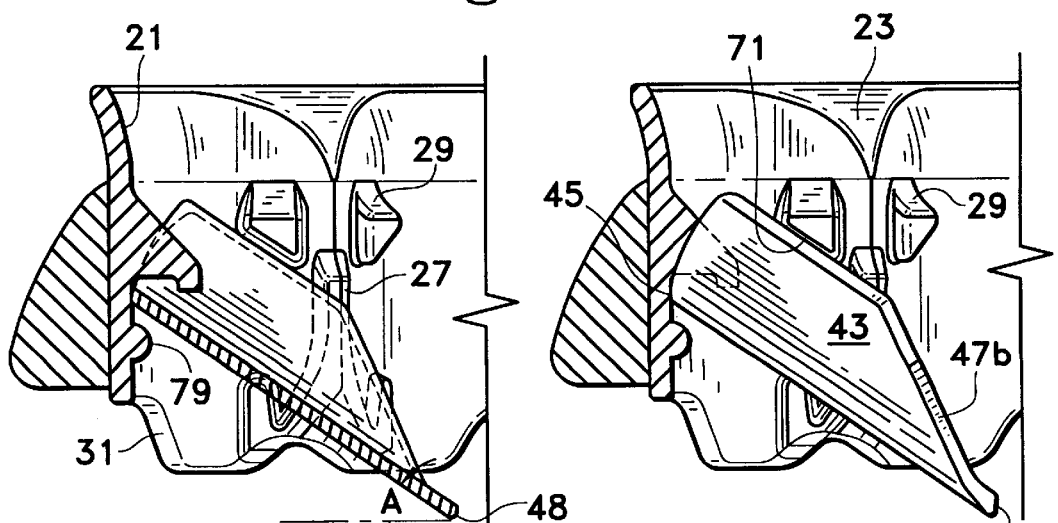

TRILEAFLET HEART VALVE

FIELD OF THE INVENTION

The present invention relates to mechanical heart valve prostheses and, in particular, to an improved trileaflet prosthetic heart valve having valve members or leaflets which can open widely to provide a large central open passageway along the centerline of the valve body passageway and which are guided by pivot arrangements that assure reliable and responsive operation.

BACKGROUND OF THE INVENTION

A wide variety of mechanical heart valve prostheses have been developed to operate hemodynamically, in conjunction with the pumping action of the heart, which are designed to take the place of defective or diseased natural valves. These valves typically have valve bodies which accommodate valve members either in the form of a single occluder or in the form of multiple occluders or leaflets, which valve members generally pivot along eccentric axes to open and close a central blood flow passageway through the valve body. Alternatively, some mechanical valves utilize valve members that both pivot and translate to open and close such a central blood flow passageway.

In its open position, a prosthetic heart valve desirably provides a central blood flow passageway which is large and which has good flow characteristics so that blood flows freely therethrough without adverse boundary layer separation and with a minimum of drag. A heart valve mounted in the aortic position should be very responsive to blood flow so as to open quickly during the pumping stroke of the heart and to close quickly when the associated chamber of the heart relaxes so as to prevent substantial regurgitation of the blood. The opening and closing of the valve should also be sufficiently soft so that the patient is not disturbed by the sounds produced and so that impacts on the valve body are minimal. The heart valve must be made of materials that are biocompatible and thromboresistant, and in this regard, it is important that all surfaces be well washed by blood to prevent regions of stagnation which might lead to eventual clotting. Furthermore, the action of the valve should be such that it does not cause hemolysis (damaging of blood cells), and of course, the heart valve should be constructed to withstand countless openings and closures without the valve members jamming or escaping.

Prior art multi-leaflet heart valves have offered a variety of designs and configurations intended to address the some of the aforementioned problems. For example, U.S. Pat. No. 4,272,854 (Jun. 16, 1981) shows an early version of a bileaflet heart valve having an ear extending from each lateral side of each leaflet, which ear pivots in a recess, guided in part by a knob traveling in a longitudinal slot that is cut more deeply into the sidewall of the valve body.

U.S. Pat. No. 4,363,142 (Dec. 14, 1982) discloses a bileaflet heart valve wherein the leaflets have laterally extending ears in the form of generally oval or spherical projections that are received in recesses of complementary design.

U.S. Pat. No. 4,373,216 (Feb. 15, 1983) discloses a bileaflet heart valve wherein protrusions, extending generally radially inward from a pair of flat sidewall sections of the valve body, guide valve members which have slots in their lateral edges which fit about such protrusions. U.S. Pat. No. 4,451,937, (Jun. 5, 1984) shows a generally similar bileaflet heart valve where the pivot arrangement is formed with a reversal of these parts so that the leaflets have laterally protruding ears which are received within slots in the valve body sidewall that guide the opening and closing movements.

U.S. Pat. No. 4,308,624 (Jan. 5, 1982) discloses heart valves of both the single occluder and bileaflet type having curved valve members which both rotate and translate in moving between the open and closed positions, being guided by laterally extending ears that travel in slots. Later versions of this valve are disclosed in U.S. Pat. No. 4,357,715 wherein an elongated depression within each slot in the valve sidewall controls lateral movement within the slot, and also in U.S. Pat. No 4,443,894 (Apr. 24, 1984) wherein the slots are of kidney bean shape.

U.S. Pat. No 4,808,180 (Feb. 28, 1989) discloses a bileaflet valve wherein the leaflets each have a semi-conical shape and thus inherently provide significant resistance to blood flow through the valve in the open position. The leaflets are guided by generally C-shaped rails that protrude from the valve body sidewall and are received in recesses of complementary shape in the lateral edges of the semi-conical leaflets.

U.S. Pat. No. 5,207,707 (Jan. 16, 1992) discloses a trileaflet heart valve wherein the leaflets translate between open and closed positions guided by ears 74 which travel along curved grooves 40 carved in walls of a pivot structure 26 that are open at their downstream ends. U.S. Pat. Nos. 4,820,299 and 5,123,918 also disclose generally similar trileaflet prosthetic heart valves. The latter illustrates a construction wherein specially configured edge guide arcs are formed in the respective faces of three triangular projections that protrude from the interior surface of the valve body. These arcs extend from the downstream edge of the valve body in a circular section that swings radially inward and then back in a direction toward the interior surface of the valve body, and they guide such leaflets in moving between the open and closed positions.

Commercially developed mechanical heart valves have frequently employed valve members oriented at a significant angle to the valve centerline in the open position, so that when backflow of blood begins, it preferentially impinges strongly upon the outflow surfaces of such valve members. This arrangement initially imparts a strong pivotal force component in the direction of closing movement which contributes to prompt closing and minimal regurgitation. It is now felt that it is particularly important for a mechanical heart valve prosthesis to provide a passageway through which blood can freely flow in the open position with a minimum of drag, and to accomplish this desired objective, it is presently believed that valve members should be able to follow the flow and, when required, assume orientations parallel or nearly parallel to the longitudinal axis of the passageway. Of course, such valves should promptly close with only a small amount of regurgitation and without creating any significant cavitation.

In summary, there is a desire for trileaflet mechanical heart valves which have such improved flow characteristics in the open position, which are reliable and responsive in leaflet movement and which are designed to avoid cavitation and the likelihood of clotting. Trileaflet heart valves which meet these criteria continue to be sought.

SUMMARY OF THE INVENTION

The present invention provides mechanical trileaflet heart valve prostheses having the aforementioned desirable characteristics wherein the three valve members or leaflets can assume an open position orientation that creates a large open central passageway through the valve body, along with three outer passageways which assure adequate flushing blood flow along the outflow surfaces of the leaflets.

The three leaflets are supported within the surrounding valve bodies by complementary interconnecting means formed (a) near the downstream ends of the leaflet edges and (b) upon otherwise flat wall surfaces of three wedge-shaped projections that extend radially inward from the valve body otherwise generally cylindrical wall. These leaflets are appropriately guided with their downstream lateral edges moving along curved paths as the leaflets undergo pivotal and translational movement between closed positions and open positions in which they can assume an orientation parallel to or nearly parallel to the longitudinal axis of the central passageway through the valve body. The leaflets are preferably shaped to avoid cavitation at the instant of closing.

These pivot arrangements are constructed so as to eliminate the possibility that the downstream lateral edge regions of the leaflets may jam or stick during their opening and closing travel along such curved paths, and they include stops that are located upstream of the upstream end of each curved path against which the inflow surfaces of the leaflets abut in closed position orientation. Inward projecting retaining means having flat downstream-facing surfaces function to retain and guide upstream edges of the leaflets during closing movement, and they also confine upstream edges of the leaflet between the valve body interior wall and downstream extensions at the radially inner ends of such retaining means. In a preferred embodiment, the leaflets have a unique, generally V-shaped, cross-section with wings that flank a flat central section, and short edge sections. Guide surfaces formed in such edge sections slide along curved rail surfaces that are formed as a part of the walls of the wedge-shaped projections, and wall surfaces adjacent the downstream ends of such rail surfaces serve as stops for the edges of the leaflets that generally define the fully open position.

BRIEF DESCRIPTION OF THE DRAWINGS

FIG. 8 is a fragmentary top plan view similar to FIG. 6 with the leaflets shown in the closed position;

FIG. 8A is a fragmentary view, greatly enlarged in size, of the portion of the valve indicated in FIG. 8;

FIG. 9 is a fragmentary sectional view taken generally along the line 9—9 of FIG. 8 and with one leaflet removed;

FIG. 10 is a fragmentary sectional view similar to FIG. 9 with the illustrated leaflet shown in elevation;

DETAILED DESCRIPTION OF THE PREFERRED EMBODIMENTS

Figure 1:
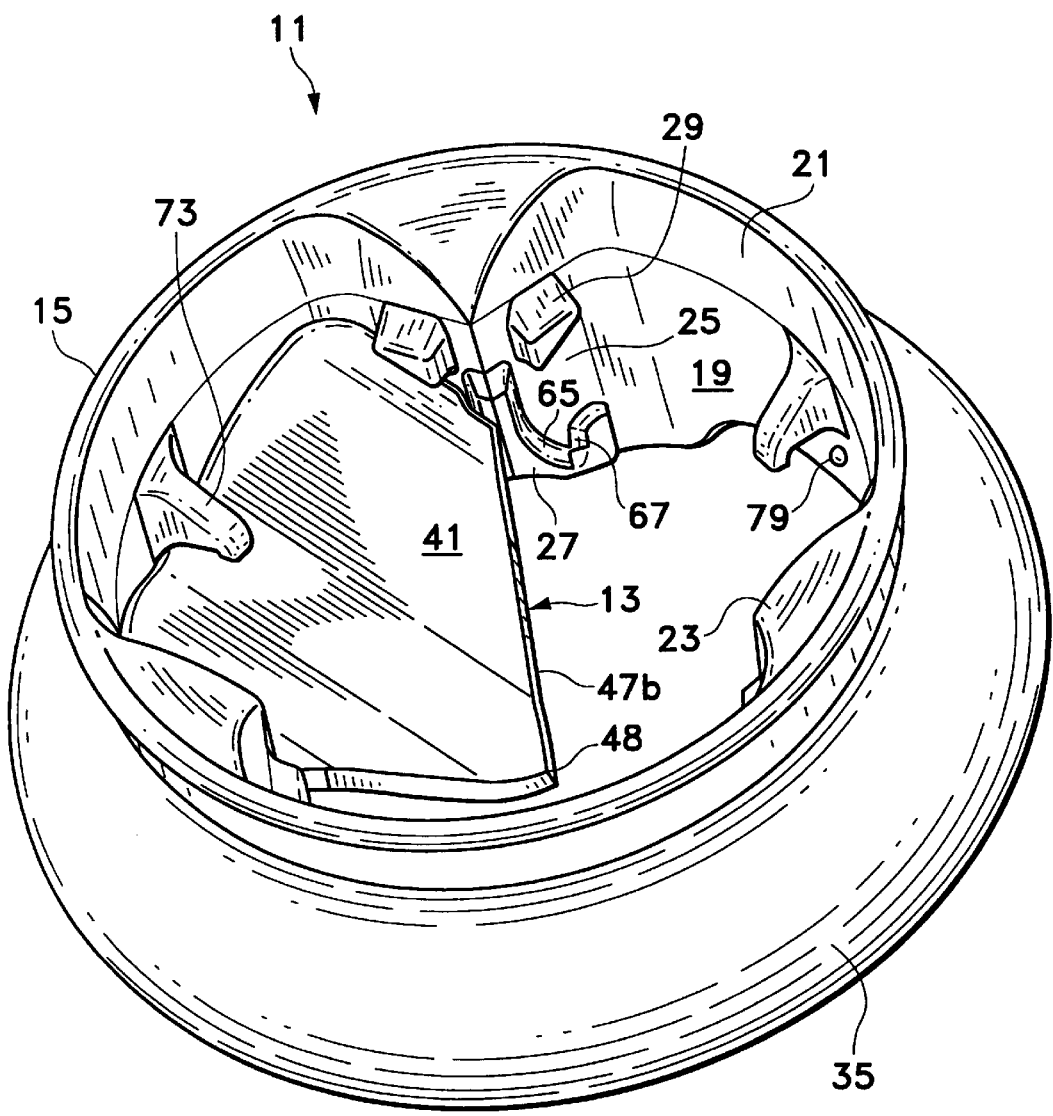
FIG. 1 is a perspective view of a trileaflet prosthetic heart valve embodying various features of the present invention, as viewed from an upstream orientation with one leaflet in the closed position and the other two leaflets removed.

Illustrated in FIG. 1 is a prosthetic heart valve 11 which embodies various features of the present invention. Heart valves of this construction exhibit improved flow characteristics as a result of relatively low pressure drops across the valve; moreover, the design of the valve body in combination with the leaflets substantially reduces boundary layer separation while also providing good washing characteristics and thereby effectively avoiding regions of stagnation and potential clotting. In addition, the pivot arrangements are such that the locations of high wear are eliminated, particularly as a result of the character of the final closing movement at the time that the forces upon the leaflets are at their highest.

Figure 5:
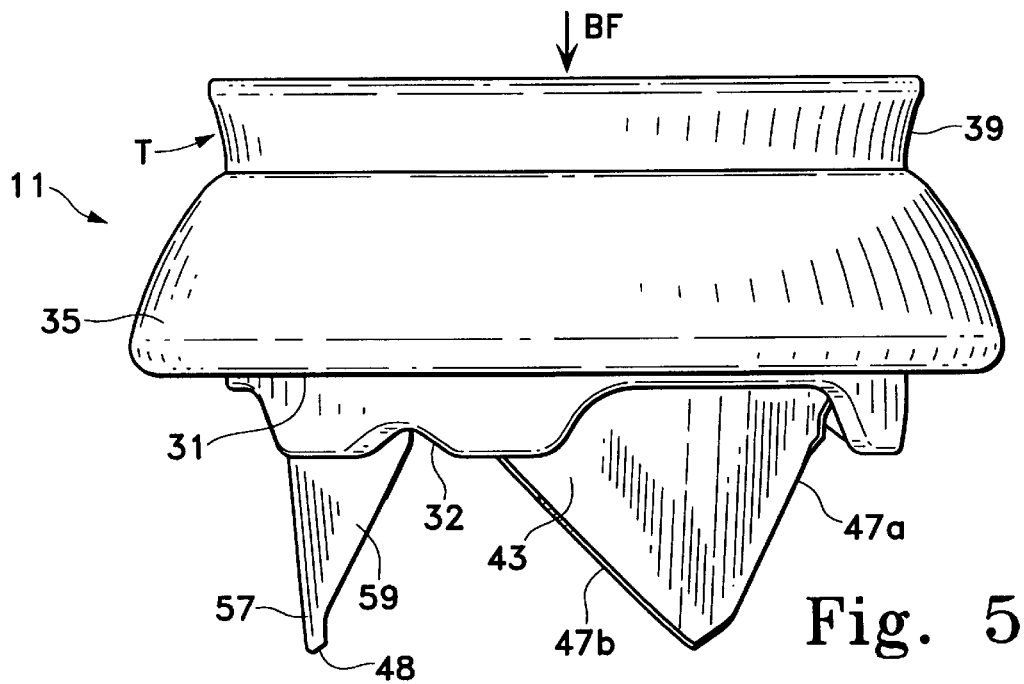
FIG. 5 is an elevation view of the heart valve of FIG. 2 with the leaflets in the open position.

The heart valve 11 includes three identical leaflets or valve members 13 which are supported within a generally annular valve body 15. The leaflets 13, which are sometimes referred to in the art as occluders, undergo generally pivoting or swinging movement and some displacement, guided by pivot arrangements which account for the supporting interengagement between the leaflets 13 and the valve body 15. The arrangement is such that the leaflets alternately open to allow the smooth downstream flow of blood in the direction of the arrow labeled BF in FIG. 5 and close to prevent substantial regurgitation or reverse flow of blood in the opposite, upstream direction.

Figure 6:
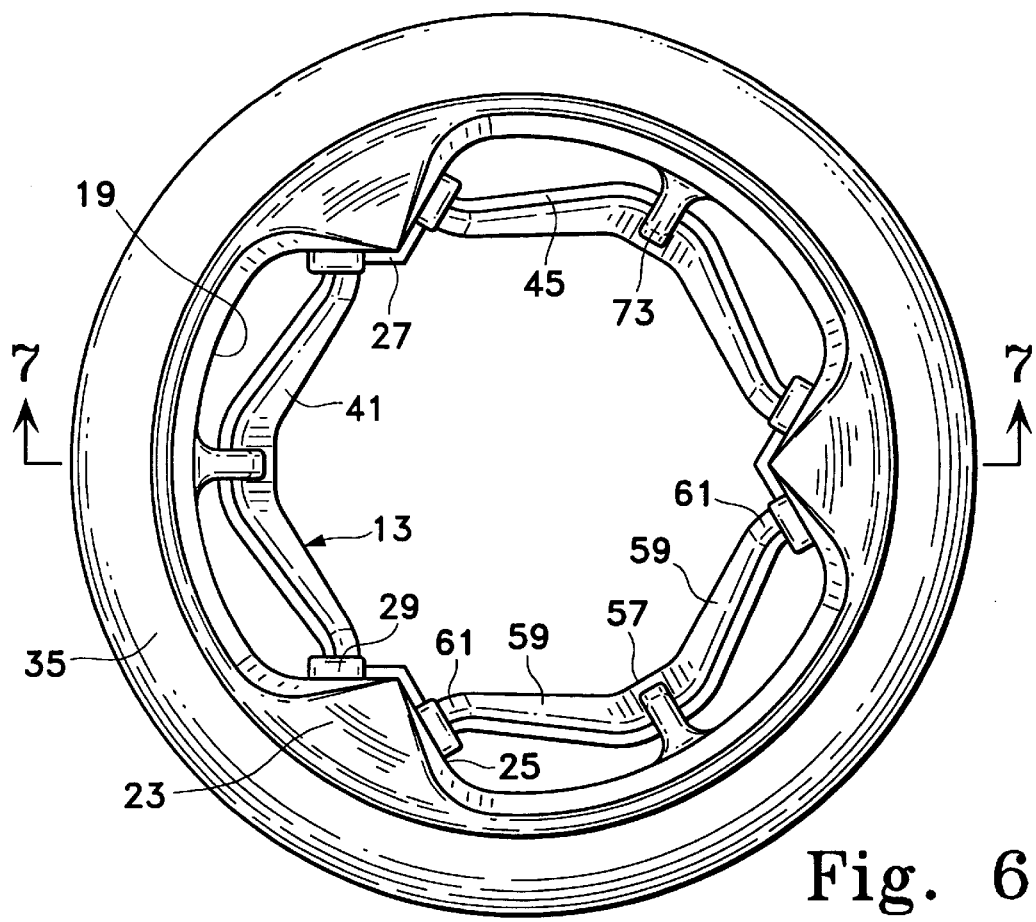
FIG. 6 is a top plan view of the trileaflet heart valve shown in FIG. 5 with all three leaflets shown in their open position.

The valve body 15 defines the blood flow passageway and has an interior wall surface 19 of nominally circular cross-section (see FIG. 6). The valve body 15 has a curved entrance region 21 (FIG. 7) at its upstream end which has been found to substantially increase streamlined flow characteristics through the valve, resulting in low turbulence and substantially no generation of thrombosis. The details of the curved entrance region 21, which extends axially for a distance not greater than about ⅓ of the average length of the valve body, are discussed hereinafter along with the operation of the valve itself.

Figure 2:
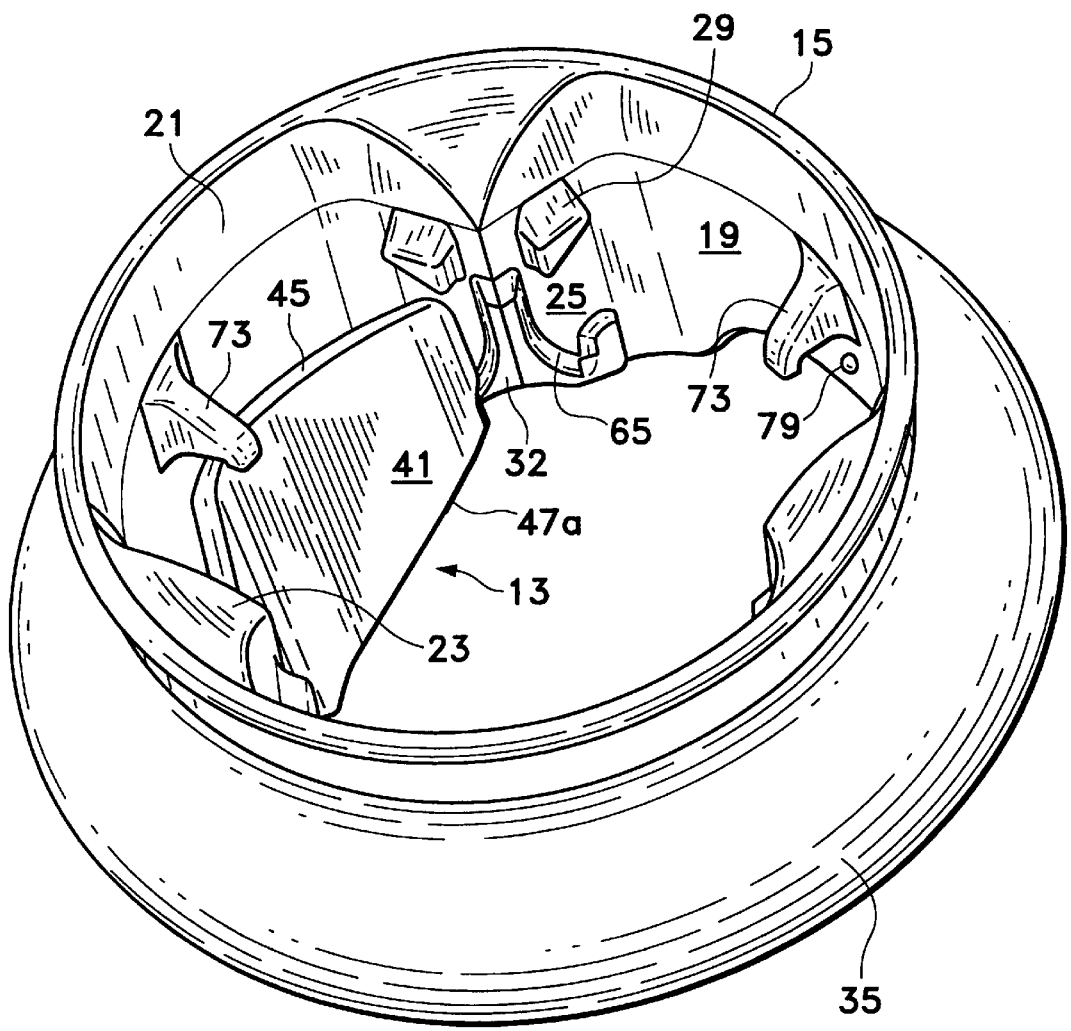
FIG. 2 is a view similar to FIG. 1 with that one leaflet shown in the open position.

The valve body 15 includes three generally wedge-shaped projections 23 which extend radially into the central passageway at 1200 intervals, as best seen in FIGS. 2 and 6. Each projection 23 has a pair of flat surface portions 25 that are aligned at about 1200 to each other. Protruding outward from the face of each of these flat surface portions is a first major protrusion 27 and a second minor protrusion 29 which is located generally adjacent the upstream end of the major protrusion 27, as best seen perhaps in FIGS. 2 and 7. These protrusions interengage with the leaflets 13 as a part of the pivot arrangement that controls the opening and closing of the valve.

The interior surface of the valve body 15 is thus generally rectilinear throughout the major portion of its axial length, i.e. downstream of the outwardly curved entrance end 21. Although the downstream end of the valve body 15 could be straight, if desired, it is illustrated as having a shallow scalloped configuration wherein three equiangularly spaced scallops 31 are formed in the circumference of the valve body at locations aligned generally with the radial projections 23, with each of the scallops 31 having a central indentation 32.

The valve body 15 has a right circular cylindrical exterior surface 33 in the region downstream of the entrance end, except for some interruption (not shown) in its central region for attaching a suture ring. A suture ring 35 is shown schematically as it would be oriented for use in implanting the heart valve 11 in the aortic position, or more particularly in a supra-aortic orientation, as explained in more detail hereinafter. For example, a mounting metal ring might be located in an accommodating groove formed in the right circular cylindrical portion of the exterior surface having such a construction that it would extend into the region of the suture ring itself to facilitate interconnection as is well known in this art. One example of such a suture ring is illustrated in U.S. Pat. No. 5,545,216, and other examples of suture rings which can be employed are described in U.S. Pat. Nos. 4,535,483 and 5,178,633. It should likewise be understood that a suitable mounting arrangement could be equivalently formed as a protruding band which would be an integral portion of the valve body itself. When the heart valve 11 is intended for implantation in the mitral position, a different shaped suture ring is used, as is well known in this art.

The valve body 15 is preferably made of a suitable material, such as pyrocarbon or pyrocarbon-coated graphite, as is well known in this art, which has sufficient resiliency that it can be deformed so as to permit the insertion of the individual leaflets 13 in their operative locations. Preferably the valve body is made from a graphite substrate coated with On-X™ pyrocarbon, which is available from Medical Carbon Research Institute, LLC, of Austin, Tex., and which is described in detail in U.S. Pat. No. 5,514,410, issued May 7, 1996.

Because of the relatively thin wall of the heart valve body 15 and the outwardly flaring entrance region 21, the exterior surface 33 of the valve body has an upstream section 39 which is a concave section of the interior surface of a hollow torus. This construction, in addition to significantly increasing the flow through the valve passageway by reducing the transvalvular pressure drop, also provides a unique opportunity for implanting the illustrated heart valve in a supra-annular orientation where the suture ring 35 sits atop the remaining tissue annulus from which the defective aortic valve was excised in the patient. In such orientation, the entrance end extends through the tissue annulus so as to be accommodated in a location where the raw edge of the tissue would be in contact with the concave toroidal surface 39 of the valve body, in the region marked "T" in FIG. 5. It should be seen that this accomplishes a dual purpose. First, it maximizes the interior diameter of the nominal cylindrical interior surface 19 that defines the valve passageway, and second, it provides an outwardly flaring surface which has the effect of directing any panus that might grow from the raw edge of the tissue annulus (following implantation) in a direction outward and away from the entrance to the valve passageway where it would potentially narrow the entrance passageway and/or interfere with the operation of the leaflets.

Figure 4:
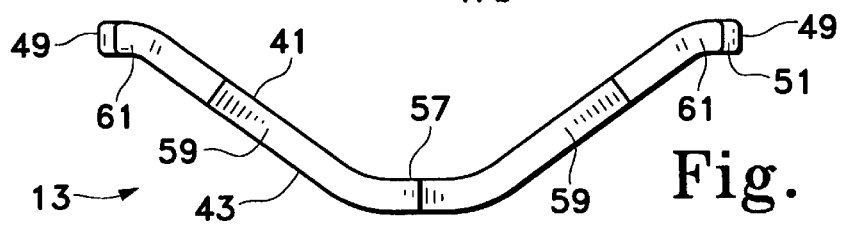
FIG. 4 is a bottom view of the leaflet of FIG. 3.

The three leaflets 13 are each identical in shape and size. Each leaflet has two rectilinear surfaces, i.e. an inflow surface 41 and an outflow surface 43, and each leaflet is preferably of substantially constant thickness (as best seen in FIG. 4) so that the surfaces 41 and 43 are parallel to each other. The inflow surface 41 is arbitrarily defined as the surface which faces upstream with the leaflets in the closed position, whereas the outflow surface 43 faces downstream. The leaflets 13 each have a major, generally arcuate, upstream edge surface 45 which is located at the upstream edge of the leaflet in the open position as best seen in FIG. 2. The arcuate edge surface 45 is configured so as to abut and seat closely against the cylindrical interior surface 19 of the valve body in the closed position orientation as seen in FIG. 8. Each leaflet also has two downstream edges that converge to meet at an inner tip 48 that lies generally adjacent the valve centerline in the closed position. Each of these edges has a radially outer planar edge surface region 47a and a radially inner edge surface region 47b which is preferably rectilinear and more preferably planar. The edges 47a and 47b are not colinear, but are oriented at an angle of about 170° or greater to each other; preferably the edge surface regions form a dihedral angle of between about 172° and about 179°. The radially outer edges are oriented at an angle of about 120° to each other and the leaflets are so proportioned that, in the closed position, the edges abut one another, as best seen in FIG. 8A; there is, however, a small gap between the radially inner regions 47b as explained below. The planar edge surface regions 47a are also formed to have an appropriate orientation to the inflow and outflow surfaces 41, 43 so adjacent edge surface regions have a flush, abutting relationship in the closed position. The edge surface regions 47a are accordingly oriented at an angle to the outflow surface 43 which is substantially the same as the acute angle A (see FIG. 9), which is the angle the rectilinear outflow surface forms with a plane perpendicular to the centerline (see reference CL in FIG. 7) through the valve body, in the closed position. This angle may be between about 15° and about 45°. However, because the approach angle of the adjacent leaflet edges is a factor in the extent to which cavitation will occur, this angle is preferably between about 15° and about 35° and more preferably between about 20° and about 30°.

In the preferred construction illustrated in FIGS. 1 to 10, the leaflets are shaped so that, in the closed position, there is contact along the radially outer edge surface regions 47a and so that there is a very slight gap between the radially inner edge surface regions 47b, as best seen in FIG. 8A where the tapering of this portion of the leaflets 13 is exaggerated for purposes of illustration. However, the planar radially inner surface regions 47b are also parallel to the centerline, so the surface regions 47a and 47b preferably form a dihedral angle of between about 172° to about 179°. Preferably, at least about the radially inner one-half of the edge 47 is tapered, and more preferably about the radially inner two-thirds of the length of the edge 47 is tapered so that the radially outer region 47a has a length equal to only about one-third of the total length of the edge 47. As a result of the tapering, the leaflets have tips 48 which are spaced from each other a distance of between about 0.001 in. to about 0.005 in. For manufacturing ease, the radially inner edge surface regions 47b are made flat so that there is a straight taper from the end of the radially outer edge surface region to the tip 48 with the edges 47b of a leaflet preferably forming a dihedral angle of between about 172° and about 179°; however, it should be understood that so long as contact between adjacent leaflets is avoided, these edge surfaces could have slightly different surface configurations. This construction serves as a positive safeguard against the occurrence of any significant cavitation, as explained in more detail hereinafter.

Figure 3:
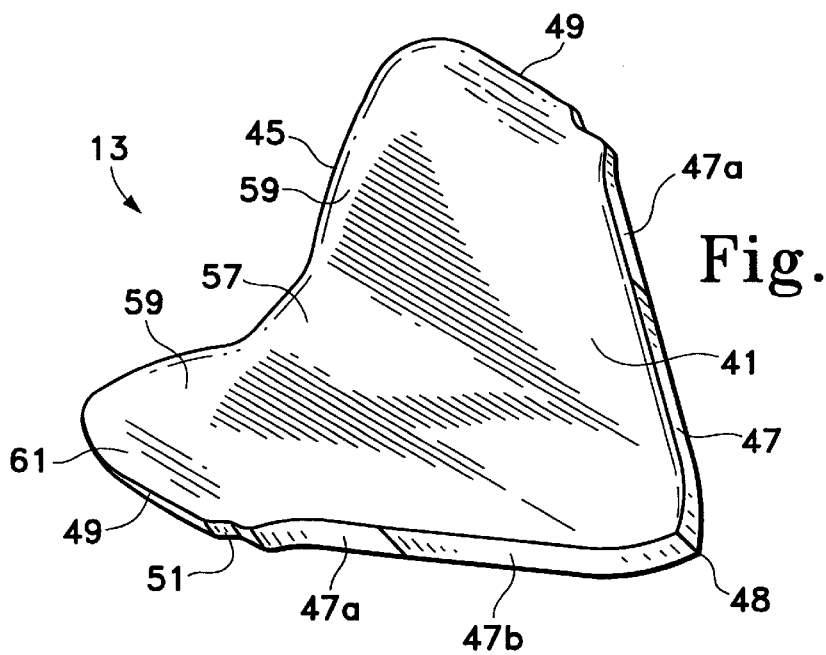
FIG. 3 is a perspective view of the leaflet of FIGS. 1 and 2.

As best seen perhaps in FIGS. 3 and 4, each leaflet 13 has a pair of planar lateral edge regions 49 located between the arcuate upstream edge and one of the downstream edge surfaces. These lateral edge surfaces 49 are notched at their downstream ends to provide a transverse guide surface 51 that is oriented so as to interengage with and slide along a complementary guide surface which forms a part of the valve body 15 as described hereinafter. The unique cross-sectional shape of the leaflets 13, as best seen in FIG. 4, is also described in detail hereinafter.

Figure 7:
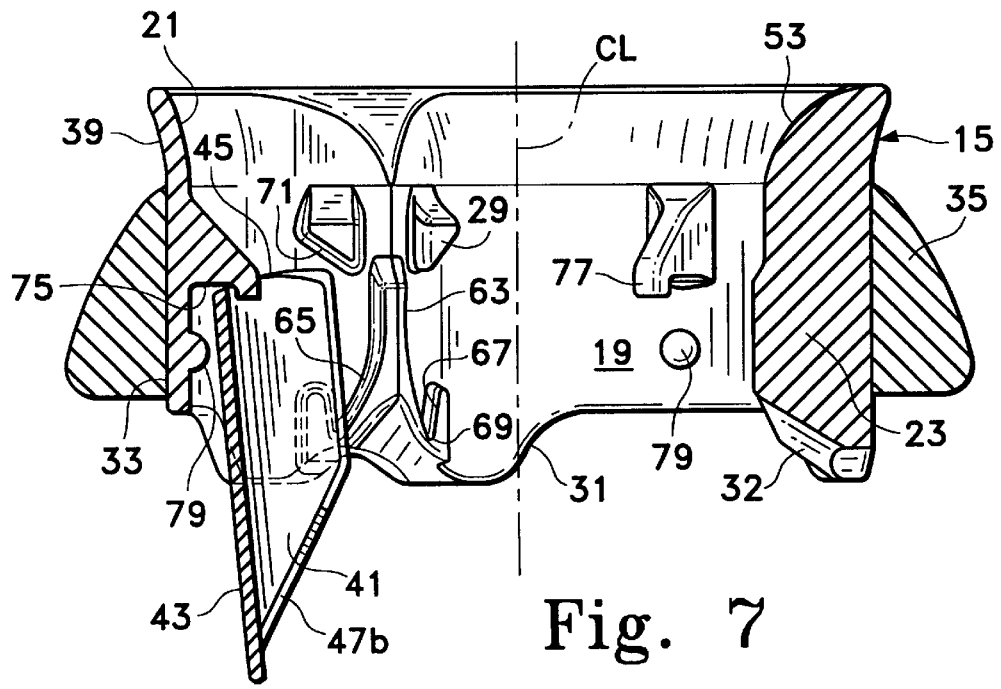
FIG. 7 is a sectional view of the trileaflet heart valve taken along the line 7—7 of FIG. 6.
Figure 11:
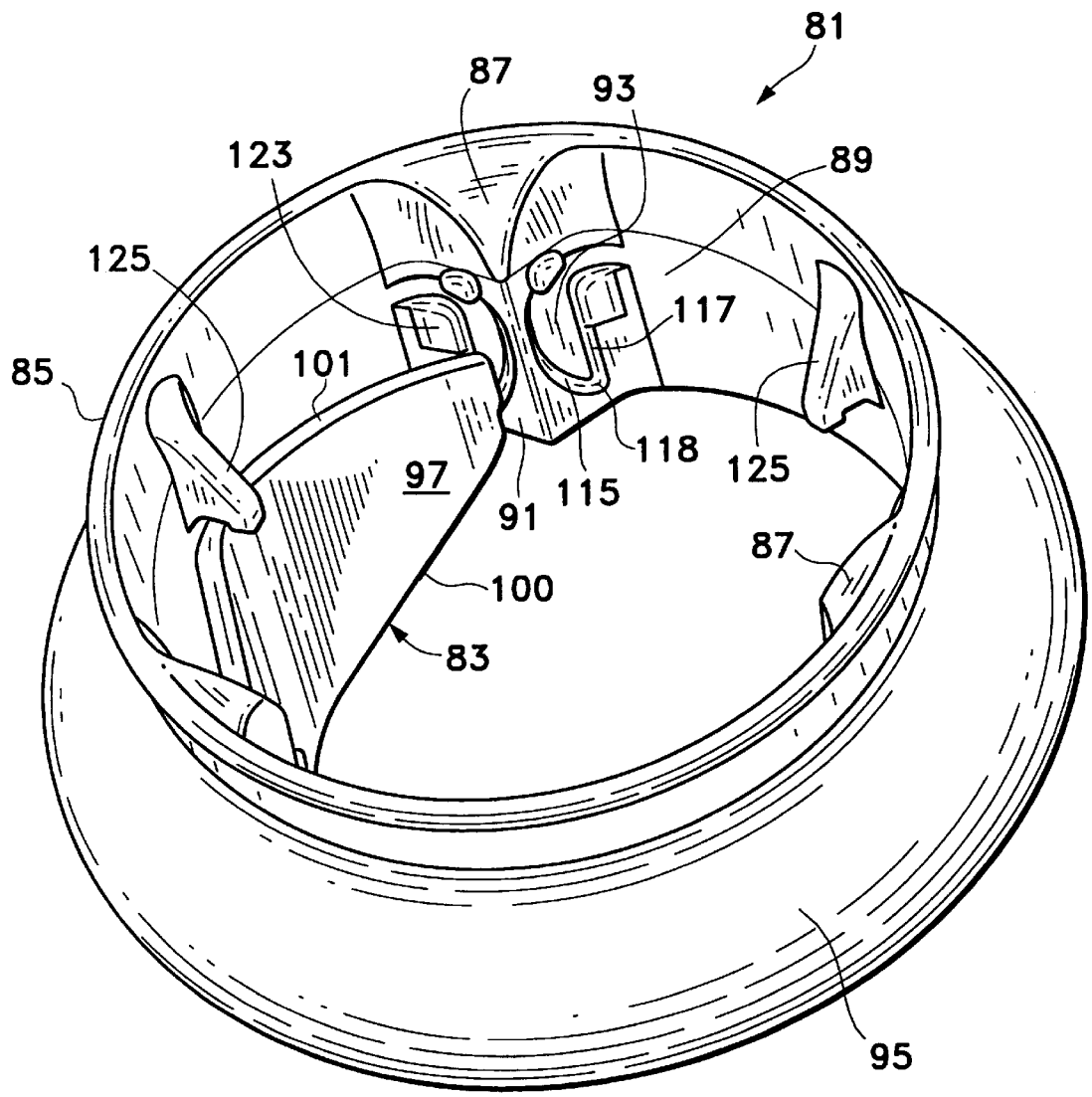
FIG. 11 is a perspective view of an alternative version of a trileaflet prosthetic heart valve embodying various features of the present invention, as viewed from an upstream orientation with one leaflet in the open position and the other two leaflets removed.
Figure 12:
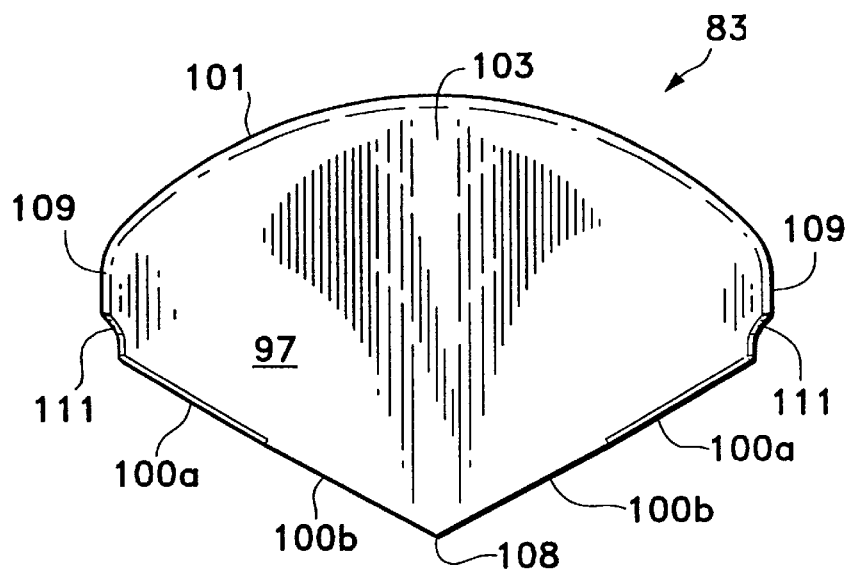
FIG. 12 is a front view of the leaflet of FIG. 11.

It can be seen from FIGS. 6 and 7 that the three projections 23 which are spaced about the circumference of the valve body constitute areas of greater wall thickness; however, the entrance end region 21 is substantially uniform about its 360° circumference, being referred to as a radial swept surface. It is preferably a surface of a section of a torus having a radius of curvature between about 28% and about 80% of the radius of the central passageway, as described in U.S. Pat No. 5,641,324 and WO 96/36299, and its downstream end is preferably tangent to the major interior right circular cylindrical surface of the valve passageway so that the internal diameter of the torus is essentially equal to the interior diameter of the valve passageway. In order to minimize the disruption of the flow through the valve, the upstream ends of the three projections 23 are provided with curved surfaces 53 which generally transition to and from the toroidal surface of the major portion of the entrance region, as best seen perhaps in FIGS. 6 and 7. The overall arrangement is such that, when viewed axially, the valve body 15 is divided into three identical regions each of which accommodates a single identical leaflet 13 which substantially completely blocks that portion of the passageway in the closed position, as viewed in FIG. 8.

The leaflets 13 have a unique shape in cross-section, as best seen in FIG. 4, being generally V-shaped. Each leaflet has a flat central section 57 with a pair of wing sections 59 flanking the central section and extending laterally therefrom in opposite directions at an angle of between about 30° and about 50°. At the end of each wing section is a short, flat edge section 61, with the edge sections being parallel to the central flat section 57. This unique cross-sectional shape of the leaflets, as best seen in FIG. 6, widely opens the central flow passageway through the valve during normal downstream flow while still channeling sufficient flow to the region between the outflow surfaces of each leaflet and the interior surface 19 of the valve body, particularly in the regions where the pivot arrangements are located to assure there is good flushing which avoids areas of stagnation that could lead to clotting. This is seen in FIG. 6 where the expanded peripheral flow passageway regions are located near the six lateral edge regions of the leaflets.

The overall pivot arrangement includes an interengagement between (a) the lateral edges 49 and the transverse guide surfaces 51 of the leaflets and (b) the wedge surfaces 25 and the major protrusions 27 of the valve body. More specifically, the major protrusions 27 each have an upstream straight section 63 which leads to a downstream arcuate section 65 which terminates in an open position stop that essentially defines the orientation of the leaflet in the open position, as best seen in FIG. 7. More specifically, the upstream section 63 and the arcuate downstream section 65 are formed by a continuous rail having a rectilinear surface that is generally transverse to the flat surface 25 of the wedge, and the transverse guide surfaces 51 of the leaflets are angularly oriented so as to slide in juxtaposition with the rectilinear surfaces of these continuous rails. At the downstream end of each arcuate downstream section 65, there is formed a crotch 69 which serves as the transition to the open position stop 67. The minor protrusions 29, which serve as the closed position stops, are formed with downstream surfaces 71 that are appropriately angularly oriented so that the flat lateral edge sections 49 of the leaflets will a but thereagainst, precisely orienting the leaflets in the closed position as illustrated in FIG. 10.

In addition to the protrusions 27 and 29, the valve body includes retaining means 73 associated with each leaflet in the form of an abutment which projects radially from the interior cylindrical wall 19 of the valve body at locations spaced equidistantly between each pair of wedge-like protrusions 23 so as to be aligned with the short central flat sections 57 of one of the leaflets when the leaflets are installed in the valve body. Each such abutment has a downstream facing flat surface 75 that extends radially into the flow passageway and which terminates at a downward extension or tang 77; the surface 75 is preferably perpendicular to the centerline through the valve body. The upstream edge 45 of the leaflet slides along the flat surface 75 during at least a portion of the closing movement of the valve leaflet. Thus, the retaining abutments 73 serve to define or limit the extent of the upstream movement of the leaflets within the valve body. To similarly limit the extent of the downstream movement of the upstream edge 45 of the leaflets, constraining bumps or protuberances 79 are provided on the valve body interior wall, in association with each retaining abutment 73, which is located downstream thereof in an upstream/downstream or axial direction. In the illustrated embodiment, a single bump 79 is associated in angular alignment with each abutment 73 and spaced appropriately downstream therefrom. However, it should be understood that a pair of bumps could be alternately provided in flanking relationship to each retaining abutment 73 at similar downstream locations, if desired. As best seen perhaps in FIGS. 9 and 10, the bumps 79 would prevent the leaflets, at the beginning of opening movement, from translating directly downstream in the orientation shown in FIG. 9, without any significant rotation occurring and possibly wedging between the wall 19 and the major protrusion 27.

The leaflets 13 may be installed in the valve body 15 in a sequential manner as by applying force such as to squeeze the valve body at diametrically opposite locations along a diameter that is generally equidistantly spaced between each pair of bearing surfaces 25 with respect to the leaflet being installed. On-X™ pyrolytic carbon has physical properties such that, even with such a radially swept entrance region, the valve can withstand some deformation so as to facilitate the insertion of the leaflets. Apparatus such as illustrated in U.S. Pat. No. 5,336,259 (Aug. 9, 1994) may be used to assist in the installation of the leaflets. As can be seen from FIGS. 6 and 8, the flat surfaces 25 of the projections which flank each one of these three regions of the valve passageway are substantially parallel to each other. Squeezing along a diameter parallel to these wall surfaces causes them to bow outward and separate further from each other, and such further slight separation coupled with the unique cross section of the leaflets allows the leaflet to be axially inserted through the outflow end of the valve body 15 and slipped into place. Once one leaflet has been installed, removal of the squeezing force allows the valve body 15 to return to its original annular configuration providing the desired minimal clearance between the flat wall surfaces 25 of the projections and the lateral edge surfaces 49 of the leaflets. The application of the squeezing force may then be sequentially shifted to a diameter 120° from the direction of its first application, and the procedure is repeated two more times in order to complete the installation. Alternatively, all three leaflets might be installed at the same time by simultaneously applying pressure at three points 120° apart. The leaflets are preferably made of graphite substrates coated with On-X™ pyrolytic carbon, as described hereinbefore with respect to the valve body, and the unique V-shaped design allows the leaflet to resiliently deform so as to slip into place over the major protrusion 27 in the regions of the crotches 69 after it is inserted so as to slide upward through the outflow end of the valve body.

With the heart valve 11 operatively installed in a patient and in the open position, the three leaflets 13 are designed to be able to assume an open position orientation wherein they are parallel or nearly parallel to the central longitudinal axis of the centerline through the valve body. By nearly parallel for purposes of this application is meant at an angle up to about 10 20 from a plane containing the pivot axis of the leaflet that is parallel to the valve centerline. The pivot axis of each leaflet as it swings from the open to the closed position is a shifting line defined by the points of contact (a) between the guide surfaces 51 and the rail surfaces 63, 65 and (b) between the upstream edge 45 and the retaining means surface 75 against which the edge slides. When the leaflets reach the open position, they will nominally assume the orientation depicted in FIG. 7 wherein the outflow surfaces 41 of the flat edge sections 61 of each leaflet are in contact with the open position stops 67, oriented from about 6° to 10° from a perfectly parallel orientation. The flared configuration of the entrance region 21 should direct the blood flow slightly radially inward toward the centerline, so the leaflets may tend to assume the orientation illustrated. However, depending upon the character of the blood flow, the leaflet shown in FIG. 7 could rotate slightly in a clockwise direction about its seat in the crotches 69 so as to approach a parallel orientation. Moreover, if desired, the stops 67 may be aligned to have an orientation closer to one parallel to the centerline.

Although the majority of blood flow is through the large central passageway which is opened by this particular leaflet design, there is also flow in the three regions between the outflow surfaces 43 of the three leaflets 13 and the interior cylindrical wall 19 of the valve body. Moreover, as can be seen from FIG. 6, these three outer passageways are largest in the regions adjacent the first and second protrusions 27, 29 and thus assure excellent flushing at these locations, eliminating regions of stagnation that could potentially lead to clotting. In this open position, the guide surfaces 51 on the leaflets reside in the crotches 69 in the major protrusions, and the upstream edge 45 of the leaflet is just slightly downstream from the flat surface 75 of the retaining abutments. In this position, as mentioned above, it is possible for the leaflet to pivot clockwise to approach a parallel orientation; however, the amount of such pivoting would be limited by engagement of the inflow surface 41 of the upper edge of the leaflet against the depending tang 77 which is located to block further rotation. Although conceivably there could be some momentary pivoting in a counterclockwise direction about the upstream end of the open position stop 67, such may be unlikely; however, in any event, such pivoting would be limited by abutment against the constraining bump 79.

Overall, as is evident from FIG. 6, a large open central flow channel is provided in the open position as a result of the leaflet's configuration and their assuming an orientation that is parallel or nearly parallel. This open central flow channel, in combination with the outwardly flared entrance end, results in a very low transvalvular pressure drop across the valve. The streamlined flow which results from this configuration insures there is nonturbulent flow in the three smaller passageway sectors between the outflow surfaces 43 of each leaflet and the interior right cylindrical surface 19 of the valve body; this assures excellent overall flow through the valve and good washing of all surfaces to prevent stagnation. Smooth nonturbulent flow, low pressure drop and the absence of stasis are a result of the combination of this particular support and guidance for the leaflets 13, together with the shape and proportioning of the valve body 15, i.e. a torroidal entrance end curvature 21 that leads to a generally cylindrical valve body having an axial length preferably at least about equal to the interior radius of the flow passageway. Moreover, the overall curved configuration of the entrance increases the stiffness of the valve body and allows the use of a valve body of thinner wall thickness, translating to a larger interior diameter for the passageway and thus less resistance to blood flow.

When the reverse or upstream flow of blood begins at the end of a pumping stroke of the left ventricle, for example, the leaflets 13 in a valve implanted in the aortic position, are subjected to drag forces tending to cause them to translate upstream, and the upstream edges 45 quickly contact the flat surfaces 75 of the retaining abutment 73. Because the major surface region of the leaflet shown in FIG. 7 is located to the right of the point of contact with the restraining means 73, a force vector results on the valve axis side of the leaflet that induces a closing moment which continues until the force of blood flow is primarily against the outflow surface which completes closing. As a result, such reverse flow of blood causes the leaflet shown in FIG. 7 to pivot counterclockwise generally about the point of engagement of its upstream edge against the flat surface 75, and this pivoting movement is guided by the leaflet guide surfaces 51 which travel along the downstream arcuate rail surfaces 65. During this pivoting, some translational movement occurs as the upstream edge 45 of the leaflet slides along the flat surface 75 until it abuts the interior cylindrical wall 19 of the valve body. As the guide surfaces 51 travel upstream along the straight section of the rail 63, the leaflet upstream edge 45 is forced radially outward if it has not already assumed this position until the inflow surfaces of the flat edge sections 61 of the leaflets abut the downstream surfaces 71 of the minor protrusions 29 which serve as the closed position stops.

In the fully closed valve, the force of the blood against the outflow surfaces 43 of the leaflets is borne mainly by the minor protrusions 29 which are located generally centrally of each of the lateral edge regions of the leaflets. With all three leaflets in this position as shown in FIG. 8, the leaflets' arcuate upstream edges 45 abut against the interior cylindrical surface 19 of the valve body, their lateral edge surfaces 49 are in juxtaposition with the flat wedge surfaces 25, the planar radially outer edge surface regions 47a of the leaflets abut one another, and the radially inner edge surface regions 47b lie juxtaposed with one another with only a slight controlled gap therebetween, thus creating an effective seal across the valve passageway.

The center tip 48 of the leaflets and the associated edge regions will be moving at the greatest velocity of any points along the edges 47 and thus will be approaching one another with the greatest relative velocity. Accordingly, the provision of minimum gaps at the tips 48 of the three leaflets and the radially inner edge surfaces 47b minimizes cavitation at the instant of closing that would otherwise potentially result in erosion and/or hemolysis. Blood is a very delicate tissue and even minor abuses caused by cavitation, turbulence and high sheer stress can cause hemolysis thrombosis and/or embolism generation at local regions. Moreover, cavitation in regions near surfaces of structural components can cause erosion and, if serious, can lead to potential valve failure. Because the radially outer edge surface regions 47a will be moving at substantially lower relative velocities, the potential creation of cavitation at these regions is not considered to be problematic. The gap should be the greatest at the locations where the relative velocity is highest, i.e. at the tips 48; here the illustrated gap is the greatest. The gap is preferably allowed to uniformly diminish as one moves radially outward from the tip along the edge 47, which is consistent with the gradual decrease in the velocity at which increments along the edge are moving. As a result, a minimal gap which avoids significant cavitation is achieved without creating an unacceptable 35 region of regurgitation leakage. Moreover, the gap required becomes smaller as the angle A (FIG. 9) approaches zero because the relative velocity at which the edges of adjacent leaflets approach each other grows smaller as the leaflets approach a closed orientation perpendicular to the centerline. However, the closing or regurgitation volume increases as the angle A decreases, so it may be preferred to design the valve so that the angle A is about 20° or greater.

At the instant when complete closure is achieved, the pressure of the blood against the outflow surfaces 43 of the leaflets is at its highest and results in controlled leakage through the regions between the guide surfaces 51 on the leaflets and the straight wall rail surfaces 63 on the valve body and a minimal amount of leakage between the tapered edges near the tips 48. By concentrating the backflow leakage primarily in the regions of the pivots, where such cleansing flow serves to positively guard against the occurrence of clotting, the operation of the valve is essentially clot-free.

When blood flow again reverses, as for example when the next pumping stroke of the left ventricle begins, the downstream force of the blood against the inflow surfaces 41 of the leaflets causes them to be displaced downstream; however, engagement of the outflow surfaces 43 against the constraining bumps 79 limits the distance the upstream ends of the leaflets can be displaced and causes pivoting to promptly begin, which in the case of the leaflet illustrated in FIG. 9 is in the clockwise direction. The path of such rotation is generally defined by the sliding of the guide surfaces 51 along the downstream arcuate rail surfaces 65, and it continues until the leaflet reaches the open position depicted in FIG. 7. Throughout this entire opening movement, the constraining bumps 79, which are preferably spherical for ease in machining, prevent direct downstream displacement from occurring that might possibly result in wedging of a leaflet.

Illustrated in FIGS. 11–16 is an alternative embodiment of a prosthetic trileaflet heart valve 81 which is generally similar to that hereinbefore just described. The heart valve 81 includes three identical leaflets 83 which are supported within a generally annular valve body 85. The arrangement is generally similar to that previously described, with the main differences residing in the interengaging means at the lateral edges of the leaflets and the flanking pairs of flat surfaces that constitute the sidewalls of three triangular projections 87. The valve body 85 has an interior surface 89 generally the same as that of the valve body 15 except for the absence of any constraining bumps 79 and the fact that it is shortened somewhat in axial length. Also contributing to the shortening in the axial length is the inclusion of only a very shallow scalloping so that the downstream edge of the valve body 85 has only very slight undulations.

Figure 15:
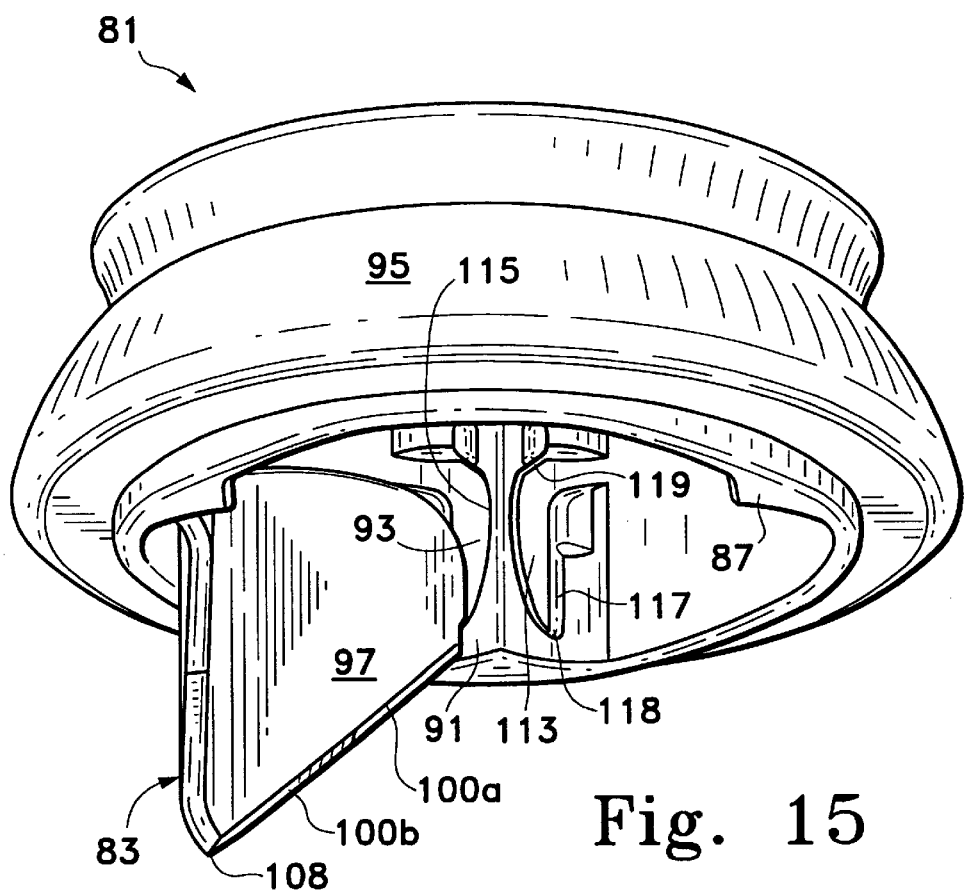
FIG. 15 is a downstream perspective view of the heart valve of FIG. 11 with the one leaflet in the open position.
Figure 16:
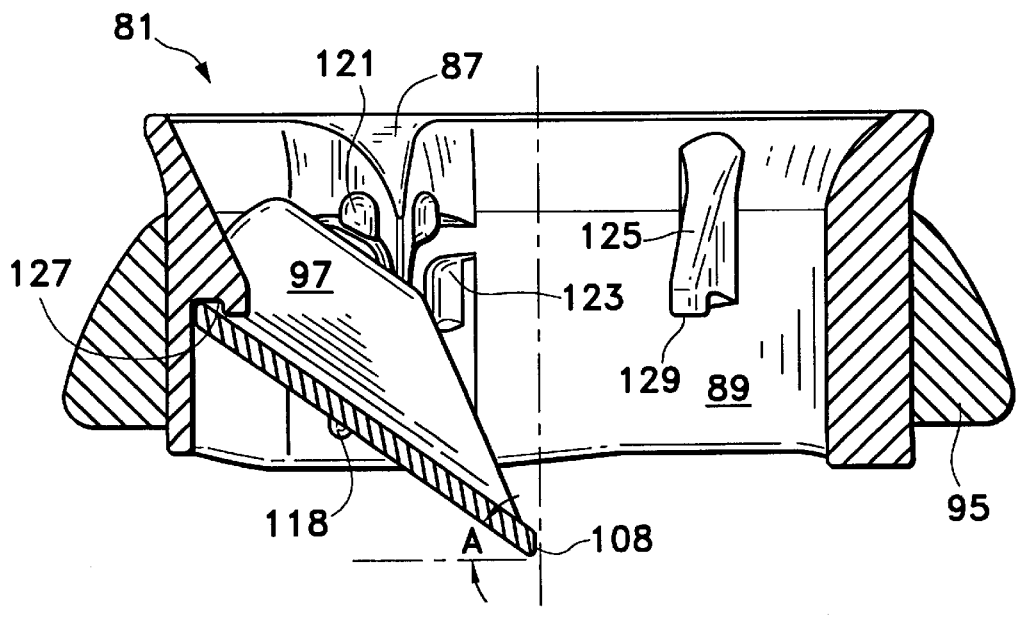
FIG. 16 is a sectional view of the trileaflet heart valve of FIG. 11 similar to FIG. 9.

As in the heart valve 11, the protrusions 87 have flat surfaces 91 aligned at 120° to each other; however, instead of having a major protrusion extending outward from these flat surfaces, the counterparts of such rail surfaces are formed as sidewall surfaces of shallow cavities 93 in the flat surfaces 91, as best seen perhaps in FIG. 15. The entrance end and the exterior surface of the valve body which supports a suture ring 95 are as described hereinbefore.

Figure 13:
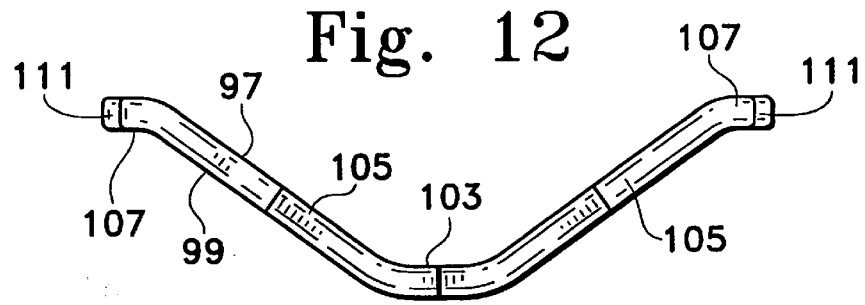
FIG. 13 is a bottom view of the leaflet of FIG. 12.
Figure 14:
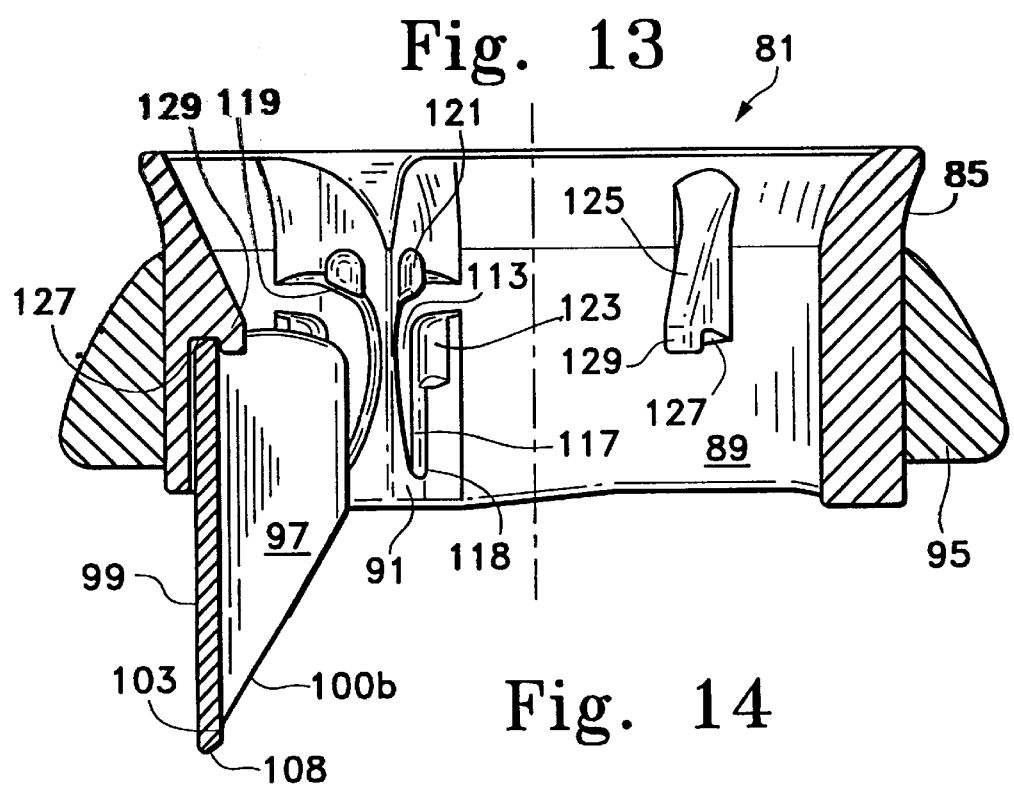
FIG. 14 is a fragmentary sectional view of the FIG. 11 valve generally similar to FIG. 7 and with one leaflet in the closed position.

The three leaflets 83 are identical in size and shape and closely resemble the leaflets 13, with some differences at the lateral edges and along the downstream edges. More specifically, the leaflets each have a rectilinear inflow surface 97, a rectilinear outflow surface 99, a pair of converging downstream edges 100 and an upstream edge 101 generally similar to the edge 45. As best seen in FIGS. 13 and 14, the leaflets have a similar, generally V-shaped cross-section with a flat central section 103, a pair of wing sections 105 and a pair of edge sections 107 that are parallel to the central section 103. Although this unique cross-sectional shape is preferred, the leaflet 83 might instead be a section of a tube of elliptical cross-section.

As in the case of the leaflets 13, the leaflets 83 are similarly tapered at the radially inner regions of their converging downstream edges 100. In the illustrated embodiment, the edges 100 have flat radially outer edge surface regions 10a which are at an angle of about 120° to each other and which extend for a distance of about one-half of the length of the edge 100. The radially inner regions are tapered so as to provide a pair of flat edge surface regions 100b which converge toward tips 108 and which are arranged at an angle to each other of greater than 120°, preferably between about 121° and 125°. As in the case of the leaflets 13, in the closed orientation, the tips 108 are spaced between about 0.001 in. to about 0.005 in. from one another, but preferably not greater than 0.003 in. As explained hereinbefore, the slight gaps between the radially interior regions of the triangular leaflets effectively counteract cavitation and are aided by designing the valve so the angle A is fairly small.

The leaflets 83 have a pair of parallel lateral edges 109 which are notched at their downstream ends to provide transverse guide surfaces 111. Aside from a slight difference in axial length, the main difference between the leaflets 83 and the leaflets 13 is that the lateral edge surfaces 109 bear against base walls 113 of the cavities 93 instead of against the flat surfaces 91 of the triangular projections 87. To provide the guide surfaces complementary to the guide edge surfaces 111, the cavities 93 are provided with flat base walls 113, curved sidewalls 115 that serve the guide function of the rail surfaces 65, straight radially outer sidewalls 117, which are located generally radially outward from the curved sidewalls and interconnected therewith at their downstream ends at a crotch 118, and an upstream diagonal sidewall 119. The cavities 93 are open at radially outward locations at their upstream ends to promote washing. Because the cavities or sockets 93 preferably have only a shallow depth, e.g. about 0.015 inch, closed position stops 121 are provided along the upstream diagonal sidewalls 119, and arcuate fulcrums 123 are provided at the upstream ends of the radially outward sidewalls 117 of the cavities. As in the case of the valve 11, the valve body 85 is formed with restraining means 125 which has a downstream surface 127 that is generally perpendicular to the centerline through the valve body and a downstream extension or tang 129 at its radially inward end.

With the leaflets 83 installed in the valve body, the lateral edges thereof are respectively received within the shallow cavities 93. Depending upon the manufacturing tolerances of the leaflets and the valve members, either the flat edge surfaces 109 of the leaflets may bear against the flat base walls 113 of the cavities, or the parallel sidewalls of the notches that create the guide surfaces 111 may bear against the flat surfaces 91 of the triangular projections. Moreover, the upstream edges 101 of the leaflets are located in juxtaposition with the flat downstream surfaces 127 of the restraining means 125.

As best seen in FIG. 14, the design and proportioning are such that the rectilinear surfaces of the leaflets 83 are essentially parallel to the centerline of the valve when the leaflets are in the full open position. In this orientation, the upstream edge 101 of each is in juxtaposition with the flat downstream surface 127 of the restraining means, the inflow surface of the flat center section 103 may abut the downstream extension or tang 129, and the guide surfaces 111 at the downstream end of the edge sections of the leaflet reside in the crotches 118. The outflow surfaces of the edge sections 107 of the leaflets abut the straight sidewall surfaces 117 of the cavities, thus establishing this parallel alignment when the guide surfaces 111 reside in the crotches 118. This orientation is stable because the tangs 129 prevent clockwise movement of the leaflets, and because the drag of the downstream flow of blood essentially prevents counterclockwise rotation, which would require the leaflet guide surfaces 111 to slide upstream along the curved guide walls 115.

When reverse or upstream flow of blood begins, as in the case of the leaflets 13, the drag of the upstream flowing blood against the surfaces creates a force vector on the valve axis side of the leaflet similar to that described with respect to the leaflets 13 that induces a closing moment which causes the leaflet shown in FIG. 14 to pivot counterclockwise. As a part of the closing movement, the upstream edge 101 of the leaflet translates slightly as it slides along the flat downstream surface 127 until it abuts the interior wall surface 89 of the valve body, while the guide surfaces 111 are sliding upstream along the arcuate path provided by the curved guide sidewall surfaces 115 of the cavities. When the guide surfaces 111 reach the upstream ends of the curved sidewalls, the leaflets have assumed the orientation depicted in FIG. 16 where the inflow surfaces of edge sections 107 of the leaflets are abutting contact with the diagonal sidewalls 119 and the closed position stops 121, and where the upstream edges 101 of the leaflets are in sealing engagement against the cylindrical interior wall surface 89 of the valve body. The sealing arrangement is essentially as described with respect to the leaflets 13 in the valve 11, with the inflow surface of the upstream edge of the leaflet just downstream of and out of contact with the restraining means 125. In the closed position illustrated in FIG. 16, the rectilinear surfaces of the leaflets again have an attitude of about 30–35° (angle A, FIG. 16), the edge surface regions 100a abut one another, and there is a slight gap between the edge surface regions 100b.

When blood again reverses and is now flowing in the downstream direction, the downstream force of the blood against the inflow surfaces 97 displaces the leaflets downstream, causing the outflow surface portions of the leaflet edge sections 107 to contact the arcuate upstream surfaces of the fulcrums 123. This causes a pivoting to occur in the opening direction (the leaflet 83 shown in FIG. 16 rotates clockwise) as the edge sections 107 slide along the facing surface of the fulcrums 123. The upstream edge 101 of each leaflet is of course confined between the interior wall 89 of the valve body and the downstream extensions 129 during the period when such relative movement is occurring in the upstream portions of the cavities.

In addition to the leaflets sliding along the fulcrums 123, their movement may be guided by the sliding travel of the guide surfaces 111 along the curved sidewall surfaces 115 of the cavities opening movement ultimately ends with the leaflets aligned parallel to blood flow and the centerline of the valve body, with the guide surfaces 111 seated in the crotches 118, and with the outflow surfaces of the leaflet edge sections abutting the flat sidewall surfaces 117 of the cavities. Thus, it can be seen that the movement of the leaflets 83 in the heart valve 81 closely resembles the movement of the leaflets 13 in the heart valve 11 described hereinbefore.

Because blood is a very delicate substance and even minor abuses caused by turbulence and high shear can result in thrombosis or emboli generation at local regions of stagnation, it is very important that cavitation and excessive turbulence coupled with high shear stresses and local regions of stasis be avoided. The foregoing valve design has been found to excellently fulfill such requirements. The employment of leaflets with rectilinear surfaces that are essentially free to follow downstream blood flow and easily orient themselves in alignment with momentary flow patterns can minimize the turbulence associated with the leaflets themselves.

The slight tapering of the radially interior edges of the leaflets effectively eliminates any troublesome cavitation, which can be aided keeping the angle A fairly small.

By confining substantially all of the functionally engaging surfaces that define the curved paths of opening and closing movement of the leaflets to regions which are located in the main bloodstream pathway through the valve body, excellent cleansing of these functional components is assured, thus removing a major area of concern in any mechanical heart valve. By limiting the final portion of the closing movement of the leaflets to one of substantially only pivoting about the upstream edges of the leaflets, the likelihood of occurrence of severe localized wear at particular points of contact when the force of the leaflet is near its maximum becomes greatly diminished. The overall design of the valve is such that gross hemodynamics in terms of energy loss per cardiac cycle are completely acceptable and are considered to be superior to those of mechanical heart valves that are presently commercially available.

Although the invention has been described with respect to certain preferred embodiments, which include what is presently considered to be the best mode for carrying out the invention, it should be understood that various changes and modifications that would be obvious to one having the ordinary skill in this art may be made without departing from the scope of the invention which is defined by the claims appended hereto. For example, as earlier indicated, the invention is not limited to interengaging means on the side surfaces of the three wedge-shaped projections in the form of protruding rails; instead, slots provided in the flat side surfaces may receive the lateral edge regions of the leaflets. Instead of using the preferred, generally V-shaped leaflet designs, leaflets in the form of sections of tubes of arcuate cross-section having short planar edge sections, or having laterally extending tabs or the like at their edges, could instead be employed; for example, the main body sections of such leaflets could be in the form of sections cut from tubes of elliptical cross-section. Furthermore, although for purposes of manufacture, it is preferred that the leaflets be of substantially constant thickness, if desired, the thickness of the leaflets could vary laterally across the leaflets or could alternatively vary in an axial direction. The disclosures of all U.S. patents mentioned herein are incorporated herein by reference. Particular features of the invention are emphasized in the claims which follow.

What is claimed is:

1. A multiple leaflet mechanical prosthetic heart valve which comprises:

a tubular valve body having an interior wall surface of generally circular cross-section which defines a central passageway for blood flow therethrough with a central longitudinal axis extending therethrough in an upstream-downstream direction, at least three relatively rigid leaflets mounted within said valve body on pivot means so as to alternately pivot between an open position to permit blood flow downstream through said valve body and a closed position to prevent blood flow upstream therethrough, each of said leaflets having a pair of converging edges that meet at an inner tip which lies generally adjacent said central axis in the closed position, each said edge lying in juxtaposition with the facing edge of an adjacent said leaflet in the closed position, and a major arcuate edge which lies in juxtaposition with said generally circular cross-section interior wall of said valve body in the closed position, and said converging edges of each said leaflet being shaped so that the radially outer regions of each converging edge interengage with the corresponding portion of said adjacent leaflet, while at least about the radially inner one-half of said converging edge is spaced from the corresponding region of said adjacent leaflet, said inner tips of said multiple leaflets being spaced from and out of contact with one another in the closed position.

2. The prosthetic valve according to claim 1 wherein said converging edges each have a straight radially outer region and a straight radially inner region, which regions are not colinear but are aligned at an obtuse angle to each other greater than about 170°.

3. The prosthetic valve according to claim 2 wherein each said radially outer edge region has a surface which is substantially rectilinear, being composed of lines which are substantially parallel to said valve body central axis in the closed position.

4. The prosthetic valve according to claim 3 wherein both said radially outer and radially inner edge surface regions are flat.

5. The prosthetic valve according to claim 4 wherein said planes of said radially outer and inner edge surface regions are aligned at a dihedral angle of between about 172° and about 179°.

6. The prosthetic valve according to claim 4 wherein there are only three leaflets and wherein said two radially outer regions of each said leaflet lie in planes which are aligned at an angle of about 120° to each other.

7. The prosthetic valve according to claim 6 wherein said two radially inner edge surface regions of the converging edges of each leaflet lie in planes which form a dihedral angle of between about 121° and about 125°.

8. The prosthetic valve according to claim 2 wherein each said radially outer region constitutes at least about one-third of the total length of said converging edge.

9. The prosthetic valve according to claim 2 wherein each said radially outer region constitutes about one-half of the total length of said converging edge.

10. The prosthetic valve according to claim 2 wherein each said radially outer region constitutes about one-third of the total length of said converging edge.

11. The prosthetic valve according to claim 1 wherein said inner tip of each of said leaflets is spaced between about 0.001 inch and about 0.003 inch from said inner tip of any other of said leaflets in the closed position.

12. The prosthetic valve according to claim 1 wherein said relatively rigid leaflets are formed of pyrolytic carbon and have rectilinear outflow surfaces, and in the closed position said rectilinear surfaces are oriented at an angle of about 30° or less to a plane perpendicular to the central axis of said central passageway of said tubular valve body.

13. The prosthetic valve according to claim 1 wherein there are only three of said leaflets.

14. The prosthetic valve according to claim 13 wherein said valve body has a generally circular cylindrical interior surface which is interrupted by three equally spaced-apart projections, which projections extend radially inward into said central passageway and contain means interengaging with said three leaflets to establish the pivoting movement thereof.

15. A trileaflet prosthetic heart valve which comprises:

a tubular valve body having an interior wall surface of generally circular cross-section which defines a central passageway for blood flow therethrough with a central longitudinal axis extending therethrough in an upstream-downstream direction, said valve body having a generally circular cylindrical interior surface which is interrupted by three equally spaced-apart projections, which projections extend radially inward into said central passageway, three leaflets mounted within said valve body and interengaging with pivot means formed on said projections so as to alternately open to permit blood flow downstream through said valve body and close to prevent blood flow upstream therethrough, each of said leaflets having a pair of converging edges that meet at an inner tip which lies generally adjacent said central axis in the closed position, each said edge lying in juxtaposition with the facing edge of an adjacent said leaflet in the closed position, and a major arcuate edge which lies in juxtaposition with said generally circular cross-section interior wall of said valve body in the closed position, and said converging edges of each said leaflet being shaped so that the radially outer regions of each converging edge interengage with the corresponding portion of said adjacent leaflet, while at least about the radially inner one-half of said converging edge is spaced from the corresponding region of said adjacent leaflet, said inner tips of said multiple leaflets being spaced between about 0.001 inch and about 0.005 inch from said inner tip of other of said leaflets in the closed position.

16. The prosthetic valve according to claim 15 wherein said converging edges each have a straight radially outer region and a straight radially inner region, which regions are not colinear but are aligned at an obtuse angle to each other greater than about 170°.

* * * * *